(12) United States Patent
Nowakowski

(10) Patent No.: US 7,037,341 B2
(45) Date of Patent: May 2, 2006

(54) KNEE JOINT ENDOPROSTHESIS SYSTEM

(76) Inventor: Andrej Nowakowski, Salzkotten (DE)

( * ) Notice: Subject to any disclaimer, the term of this patent is extended or adjusted under 35 U.S.C. 154(b) by 294 days.

(21) Appl. No.: 10/432,335

(22) PCT Filed: Nov. 21, 2001

(86) PCT No.: PCT/DE01/04329

§ 371 (c)(1),
(2), (4) Date: May 20, 2003

(87) PCT Pub. No.: WO02/41809

PCT Pub. Date: May 30, 2002

(65) Prior Publication Data

US 2004/0044414 A1     Mar. 4, 2004

(30) Foreign Application Priority Data

Nov. 21, 2000 (DE) ................... 100 57 675

(51) Int. Cl.
*A61F 2/38*   (2006.01)
(52) U.S. Cl. .................................. 623/20.14
(58) Field of Classification Search .......... 623/20.14, 623/20.24, 20.26, 20.27, 20.28, 20.29, 20.31, 623/20.15, 20.21, 20.22, 20.23
See application file for complete search history.

(56) References Cited

U.S. PATENT DOCUMENTS

| 4,673,408 A | * | 6/1987 | Grobbelaar | 623/20.29 |
| 5,092,895 A | | 3/1992 | Albrektsson et al. | |
| 5,609,645 A | * | 3/1997 | Vinciguerra | 623/20.28 |
| 5,782,925 A | * | 7/1998 | Collazo et al. | 623/20.28 |

FOREIGN PATENT DOCUMENTS

| DE | 91 04 680.7 | 8/1991 |
| DE | 34 29 157 | 2/1996 |
| DE | 197 08 375 | 7/1998 |
| DE | 198 16 984 | 10/1999 |
| EP | 0 183 669 | 6/1986 |
| FR | 2 630 639 | 4/1988 |
| FR | 2 630 640 | 11/1989 |
| FR | 2 677 880 | 6/1991 |
| FR | 2 702 369 | 3/1993 |
| WO | WO 89/09579 | 10/1989 |

* cited by examiner

*Primary Examiner*—Eduardo C. Robert
*Assistant Examiner*—Michael Araj
(74) *Attorney, Agent, or Firm*—Collard & Roe, P.C.

(57) ABSTRACT

A knee joint endoprosthesis system includes a femur component, two friction bearings and a tibia component. The tibia component comprises two joint surface units and a transversal support. The transversal support is implanted into the tibia at a certain distance from an upper resection surface of the tibia and the joint surface units are supported by support elements on the transversal support and are fixed thereto.

9 Claims, 1 Drawing Sheet

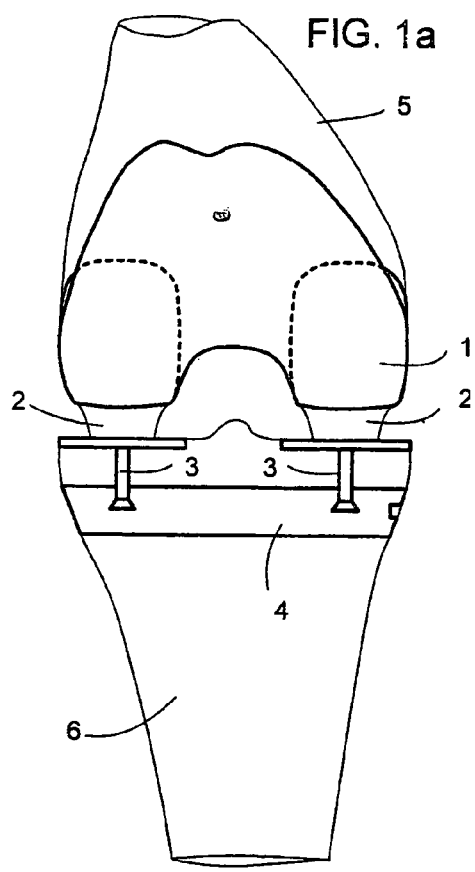
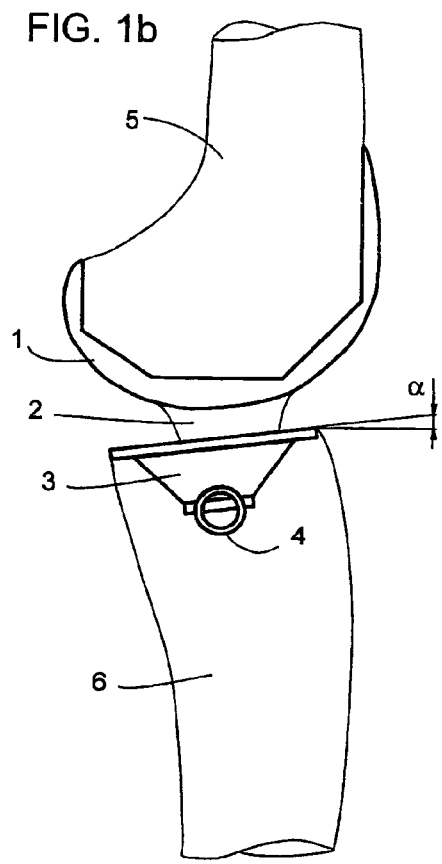
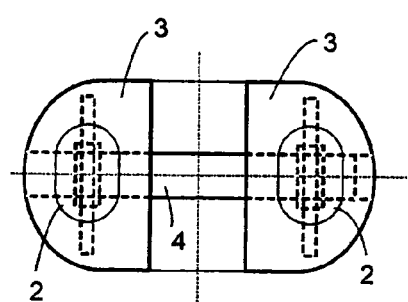
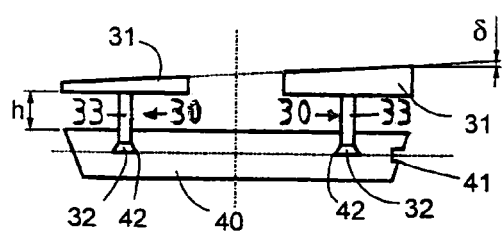

KNEE JOINT ENDOPROSTHESIS SYSTEM

CROSS REFERENCE TO RELATED APPLICATIONS

Applicant claims priority under 35 U.S.C. §119 of German Application No. 100 57 675.3 filed Nov. 21, 2000. Applicant also claims priority under 35 U.S.C. §365 of PCT/DE01/04329 filed Nov. 21, 2001. The international application under PCT article 21(2) was not published in English.

BACKGROUND OF THE INVENTION

1. Field of the Invention

This invention relates to a knee joint endoprosthesis system.

2. Prior Art

Knee joint endoprostheses are used to restore the knee-joint function after the natural knee joint is injured due to wear or damage to the bone, e.g., due to a tumor.

Knee joint endoprosthesis systems are already known from German Patent 198 16 984 A1, German Patent 197 08 375 A1, German Patent 91 04 680, French Patent 2 702 369 and International Patent WO 89/09579. In the International Patent WO 89/09579, which forms the generic state of the art, two transversal supports are integrated into the tibia at a distance from an upper resection surface of the tibia. Two joint surface units are supported, each in one recess in the transversal support via joint surface supports and are secured by means of stud screws. The recesses run axially in the transversal support and the joint surface supports can be inserted into the recesses only from above.

To have an adequate clearance for assembly of the joint surface units with the joint surface supports in the transversal supports, the bone of the upper thigh, i.e., the femur and the tibia, must be spread apart, but that is limited by the cruciate ligaments.

Therefore, with the known endoprostheses system, the anterior cruciate ligament must be resected, although it is a well-known fact that the anterior cruciate ligament is important as a central supporting pillar for the stability of the knee and also to support the physiological movement of the knee.

For implantation of these known knee joint endoprosthesis systems, resection of the anterior cruciate ligament is necessary, although the importance of the anterior cruciate ligament as a central supporting pillar in the stability of the knee as well as in supporting physiological motion of the knee is well-known.

The reasons for the known measures include stability problems with the prostheses developed so far, surgical problems due to the use of the prostheses proximally as well as the limited possibilities of adjusting the prostheses in alignment with the inclination of the tibia plateau.

SUMMARY OF THE INVENTION

The object on which this invention is based is to create a knee joint endoprosthesis system in which the tibia component can be installed and secured in the tibia in a stable position while preserving the cruciate ligaments and to thereby permit a permanent and physiologically correct mobility of the knee joint.

This object is achieved through the features in a knee joint endoprosthesis system as disclosed herein.

Refinements and advantageous embodiments are also disclosed.

The basic idea is to align and secure two individual joint surface units on a transversal support, which is introduced on the tibia side. In this way, with a high stability of the prosthesis due to its design, it is possible to preserve the cruciate ligaments. Since the joint surface units are attached to the transversal support, the correct mutual axial alignment is ensured, thus preventing premature wear of the friction bearing.

In contrast with the known solutions in which the transversal support is attached only to the upper resection surface of the tibia, integration into the tibia at a distance from the resection surface permits an especially secure anchoring.

The posterior alignment of the tibia plateau inclination, which makes a significant contribution toward the cruciate ligament tension and thus toward physiological movement is continuously adjustable as required by the knee joint to be treated.

The two joint surface units may be installed from the anterior approach, or to completely preserve the ventral corticalis, they may be installed from obliquely from the upper front. For the traditional surgical procedure, a small additional incision is necessary to introduce the transversal support.

The transversal support is preferably integrated into the tibia approximately at the center.

Because the axis of the transversal support is therefore closer to the projection of the center of gravity of the joint surface, torsional loading is prevented. In the known solutions with the connecting web, this has often resulted in material fatigue and thus breakage of the connecting web.

According to a refinement of this invention, the transversal support has a key surface or a flange on at least one axial end.

Therefore, the transversal support can be introduced into the tibia by using a tool and adjusted to set the angle for alignment of the tibia plateau inclination.

The joint surface supports preferably each consist of a tibia plateau plate and a support element perpendicular to the former or bent to the perpendicular. The lower end of the support element is secured in a recess in the transversal support.

This embodiment of the support element minimizes the unavoidable countersinking of the tibia and thus largely prevents weakening of the bony substance. The main force component runs in the direction of the longitudinal axis of the support element, so that torsional, shearing and bending stresses are reduced. An inclination of the support element is taken into account when the head of the tibia tapers greatly toward the bottom.

In an advantageous embodiment, the lower end of the support element and the recess in the transversal support produce a form-fitting connection.

On assembly across the axis of the transversal support, the lower end of the support can be introduced into the transversal support and then is secured permanently with respect to the main force component.

In addition, the upper side of the tibia plateau plate forms an acute angle with its bottom side facing the upper reaction surface of the tibia.

This permits an axial correction with respect to the axis of the transversal support introduced.

The outside surface of the transversal support is preferably designed with a profiling and/or it has openings to cavities on the interior.

This makes it possible for bony substance to grow into the profile or the openings, yielding a form-fitting connection between the bony substance and the transversal support during the healing process, which increases the secondary stability.

Furthermore, the relative position between the friction bearings and the tibia plateau plate can be variable by means of an adjustment device with guides and stops.

After implanting the transversal support, a precision adjustment of the friction bearings is possible by means of this adjustment device, to ensure optimum physiological function of the knee joint.

BRIEF DESCRIPTION OF THE INVENTION

The present invention is explained in greater detail below on the basis of one exemplary embodiment, which is illustrated in the drawing.

The drawing shows:

FIGS. 1a, b a schematic diagram of a knee joint endoprosthesis system;

FIG. 2 a top view of the transversal support tibia plateau, and

FIG. 3 a frontal view according to one embodiment of this invention with another embodiment of the joint surface units.

DETAILED DESCRIPTION OF THE INVENTION

FIG. 1a shows a femur component 1 on a femur 5, which articulates by means of two friction bearings 2 with the joint surface units 3 of the transversal support tibia plateau. The joint surface units 3 are in turn secured on the transversal support 4. The tibia plateau is implanted in a tibia 6. The femur component is a conventional shape, where it is important that the design is as congruent as possible with the friction bearing 2 in the angular area of the leg.

In addition, the friction surface of the femur component should be imaged toward the dorsal direction by multiple radii to reproduce the physiological condyles as closely as possible, because the tension of the cruciate ligaments is also determined in this way. The design of the bearing between the joint surface units 3 and the friction bearings 2 can be a simple flat surface or it can be altered by stops or guides to increase stability.

All bearing surfaces of the prosthesis components from the allowed materials toward the bone are designed according to the conventional methods so that the bone can grow into it and thus develop the secondary stability. To increase the primary stability, the transversal support 4 may be provided with an outside thread.

FIG. 1b shows the side view of FIG. 1a. It is important here that the angle α to the alignment of the tibia plateau inclination in the dorsal direction is copied precisely, this angle α is determined preoperatively by radiological diagnostic methods or intraoperatively by a suitable method, in order to maintain the physiological cruciate ligament tensions during the movement process.

The tibia-side friction surface of the friction bearings 2, shown in FIG. 2, can be designed to be smaller than the friction surface on the femur side because of the full contact surface. Therefore, severe wear on the friction bearings 2, which are preferably made of UHMW polyethylene, is not to be expected here in contrast with the friction surface on the femur side, which decreases with flexion due to the condyle radius becoming smaller.

In embodiments with stops or guides, the size of the friction surface of the friction bearings 2 on the tibia side may have to be increased, if necessary.

FIG. 3 again shows the essential components of the transversal support tibia plateau having two joint surface units 3, consisting of 30 to 32, and a transversal support 4, consisting of 40 to 42.

The height h, which is determined by a suitable choice of length of the joint surface support 30, determines the tight fit and thus also provides a high primary stability.

If an additional correction of the axis relative to the transversal support 4 implanted is to be necessary intraoperatively, this can be accomplished through another embodiment of the joint surface units by changing the varus/valgus angle δ. The connection between the joint surface units 3 and the transversal support 4 is shown as an embodiment with a dovetail groove 32, 42. Other state-of-the-art joining techniques can also be used here.

The basic shape of the transversal support 40, shown in FIG. 3 as an embodiment having a round hollow profile, can also be designed as a screw, a hollow screw or some other profile or hollow profile, which may have openings to allow bone to grow into them. The length should be selected so that it is anchored in the corticalis of the tibia on both sides.

When the head of the tibia tapers greatly, it may be necessary to design the alignment between the joint surface support 30 and the joint surface 31 so they are not perpendicular to one another. The transversal support flange 41 is used for introducing the transversal support 4 into the tibia and for adjusting the angle α for the alignment of the inclination of the tibia plateau dorsally. Through a suitable shape, the resection tool can be aligned with and attached to the tibia joint surface resection.

What is claimed is:

1. A knee joint endoprosthesis system comprising:
   a femur component;
   two friction bearings and;
   a tibia component,
   wherein the tibia component comprises two joint surface units and a transversal support, the transversal support adapted to be integrated into a tibia at a distance from an upper resection surface of the tibia, and the joint surface units being supported on and attached to recesses in the transversal support via joint surface supports, wherein the recesses run across an axis of the transversal support and are accessible from a front for insertion of the joint surface supports.

2. The knee joint endoprosthesis system according to claim 1, wherein the transversal support is adapted to be integrated into the tibia approximately at a center of the tibia.

3. The knee joint endoprosthesis system according to claim 1, wherein the transversal support has a key surface or a flange on at least one axial end.

4. The knee joint endoprosthesis system according to claim 1, wherein the joint surface supports each comprise a tibia plateau plate and a support element perpendicular to the tibia plateau plate, and a lower end of the support element is secured in a recess in the transversal support.

5. The knee joint endoprosthesis system according to claim 4, wherein a lower end of the support element and the recess of the transversal support create a form-fitting connection.

6. The knee joint endoprosthesis system according to claim 4, wherein an upper side of the tibia plateau plate forms an acute angle with a bottom side of the tibia plateau plate which faces an upper resection surface of the tibia.

7. The knee joint endoprosthesis system according to claim 1, wherein an outside surface of the transversal support is designed with profiling and/or has openings toward interior cavities.

8. The knee joint endoprosthesis system according to claim 4, wherein a relative position between the friction bearings and the tibia plateau plate is variable by means of an adjusting device having guides and stops.

9. A knee joint endoprosthesis system comprising:
 a) a femur component;
 b) two friction bearings; and
 c) a tibia component, said tibia component comprising:
  i) two joint surface units; and
  ii) a transversal support adapted to be integrated into a tibia at a distance from an upper resection surface of the tibia,
 wherein said joint surface units are supported on and attached to recesses in said transversal support via joint surface supports, and said recesses run across an axis of said transversal support and are ventrally accessible for insertion of said joint surface supports.

* * * * *